US012648758B2

(12) United States Patent
Miyachi

(10) Patent No.: US 12,648,758 B2
(45) Date of Patent: Jun. 9, 2026

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/455,563

(22) Filed: Aug. 24, 2023

(65) Prior Publication Data

US 2024/0081786 A1      Mar. 14, 2024

(30) Foreign Application Priority Data

Sep. 12, 2022    (JP) ................................. 2022-144651

(51) Int. Cl.
A61B 8/00          (2006.01)
A61B 8/08          (2006.01)

(52) U.S. Cl.
CPC ............ A61B 8/469 (2013.01); A61B 8/0833 (2013.01); A61B 8/0891 (2013.01)

(58) Field of Classification Search
None
See application file for complete search history.

(56) References Cited

U.S. PATENT DOCUMENTS

| | | | |
|---|---|---|---|
| 2009/0105585 A1 | 4/2009 | Wang et al. | |
| 2012/0108972 A1 | 5/2012 | Miyama et al. | |

2012/0130245 A1     5/2012  Chono
2013/0046168 A1*    2/2013  Sui ........................ A61B 8/0891
                                                              600/407
2017/0238909 A1     8/2017  Shin et al.
2019/0350561 A1*   11/2019  Ebata ................... G06V 10/993
2020/0237184 A1*    7/2020  Shigeta .............. A61B 1/00055
2021/0007710 A1*    1/2021  Douglas .............. A61B 8/5207

(Continued)

FOREIGN PATENT DOCUMENTS

| | | |
|---|---|---|
| JP | 2010-527277 A | 8/2010 |
| JP | 2012-090819 A | 5/2012 |

(Continued)

OTHER PUBLICATIONS

The extended European search report issued by the European Patent Office on Dec. 11, 2023, which corresponds to European Patent Application No. 23196787.8-1126 and is related to U.S. Appl. No. 18/455,563.

(Continued)

*Primary Examiner* — Patricia J Park
(74) *Attorney, Agent, or Firm* — Studebaker Brackett PLLC

(57)          ABSTRACT

Provided are a control method for an ultrasound diagnostic apparatus and an ultrasound diagnostic apparatus that enable a user to easily and accurately perform a diagnosis.
An ultrasound diagnostic apparatus includes: a detection target detection unit configured to detect at least one detection target captured in an ultrasound image; and a region-of-interest setting unit configured to set, in a case where a plurality of the detection targets are detected by the detection target detection unit, only for a part of the detection target among the plurality of detection targets, a region of interest including the part of the detection target.

14 Claims, 7 Drawing Sheets

(56)  References Cited

U.S. PATENT DOCUMENTS

| | | | |
|---|---|---|---|
| 2021/0186467 A1 | 6/2021 | Urabe et al. | |
| 2021/0219941 A1* | 7/2021 | Tsutaoka | G06T 7/73 |
| 2022/0079552 A1 | 3/2022 | Tek et al. | |
| 2022/0175344 A1 | 6/2022 | Matsumoto | |
| 2022/0370045 A1* | 11/2022 | Matsumoto | A61B 8/469 |

FOREIGN PATENT DOCUMENTS

| | | | |
|---|---|---|---|
| JP | 2016-195748 A | 11/2016 | |
| JP | 2020-137974 A | 9/2020 | |
| JP | 2022-179966 A | 12/2022 | |
| WO | 2011-013693 A1 | 2/2011 | |
| WO | 2019-078237 A1 | 4/2019 | |
| WO | 2019-142954 A1 | 7/2019 | |

OTHER PUBLICATIONS

"Notice of Reasons for Refusal" Office Action issued in JP 2022-144651; mailed by the Japanese Patent Office on Mar. 3, 2026.

\* cited by examiner

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

The present application claims priority under 35 U.S.C. § 119 to Japanese Patent Application No. 2022-144651, filed on Sep. 12, 2022. The above application is hereby expressly incorporated by reference, in its entirety, into the present application.

BACKGROUND OF THE INVENTION

1. Field of the Invention

The present invention relates to an ultrasound diagnostic apparatus and a control method for an ultrasound diagnostic apparatus for setting a region of interest in an ultrasound image.

2. Description of the Related Art

Conventionally, an ultrasound image representing a tomogram of an inside of a subject under examination has been acquired using a so-called ultrasound diagnostic apparatus, and a diagnosis for the subject under examination has been performed by a user such as a doctor based on the acquired ultrasound image. In order for the user to smoothly perform such an examination for the subject under examination, there is known a technique for automatically detecting an object such as an organ of the subject under examination shown in an ultrasound image. For example, JP2020-137974A discloses that a detection target inside a subject under examination is automatically detected by a machine learning model that has learned in advance a large number of ultrasound images obtained by imaging the detection target.

SUMMARY OF THE INVENTION

However, in a case where the detection target is automatically detected as disclosed in JP2020-137974A, a plurality of detection targets that should not be depicted together in the ultrasound image, such as a feces and a minor axis image of an empty rectum, may be detected together in some ultrasound images on which detection processing is performed. In this case, a user such as a doctor may not be able to accurately grasp the detection target in the ultrasound image, which may make it difficult to easily and accurately perform a diagnosis related to the detection target.

Meanwhile, among so-called intima-media thicknesses (IMTs), a so-called maxIMT, which is the thickest IMT, may be measured based on the ultrasound image. In a case where a so-called plaque is generated in a blood vessel, the maxIMT is usually measured by measuring the IMT of a site where the plaque is generated. For example, in a case where an attempt is made to automatically detect a measurement portion of the maxIMT using a technique as disclosed in JP2020-137974A, both a plaque and a non-plaque site, which is a site where no plaque is generated, may be detected. As described above, in a case where a portion other than an appropriate measurement portion is detected, the user may not be able to grasp an appropriate measurement position, which may make it difficult to easily and accurately perform the subsequent diagnosis.

The present invention has been made in order to solve such a conventional problem, and an object of the present invention is to provide an ultrasound diagnostic apparatus and a control method for an ultrasound diagnostic apparatus capable of easily and accurately performing a diagnosis.

According to the following configuration, the above object can be achieved.

[1] An ultrasound diagnostic apparatus comprising:
  a detection target detection unit configured to detect at least one detection target captured in an ultrasound image; and
  a region-of-interest setting unit configured to set, in a case where a plurality of the detection targets are detected by the detection target detection unit, only for a part of the detection target among the plurality of detection targets, a region of interest including the part of the detection target.

[2] The ultrasound diagnostic apparatus according to [1], further comprising:
  a certainty factor calculation unit configured to calculate a certainty factor for the at least one detection target detected by the detection target detection unit,
  in which the region-of-interest setting unit is configured to decide on the part of the detection target from the plurality of detection targets based on the certainty factor calculated by the certainty factor calculation unit.

[3] The ultrasound diagnostic apparatus according to [2], further comprising:
  an input device configured to accept an input operation of a user; and
  a weighting unit configured to perform weighting on the certainty factor calculated by the certainty factor calculation unit, based on the input operation of the user via the input device.

[4] The ultrasound diagnostic apparatus according to any one of [1] to [3],
  in which the plurality of detection targets are a rectum and a feces.

[5] The ultrasound diagnostic apparatus according to any one of [1] to [3],
  in which the plurality of detection targets are a prostate and a uterus.

[6] The ultrasound diagnostic apparatus according to any one of [1] to [3],
  in which the plurality of detection targets are a plaque and a non-plaque site of a blood vessel.

[7] The ultrasound diagnostic apparatus according to [6], further comprising:
  a measurement unit configured to measure an intima-media thickness of the blood vessel based on the ultrasound image,
  in which the region-of-interest setting unit is configured to set the region of interest for one of the plaque or the non-plaque site, and
  the measurement unit is configured to measure an intima-media thickness of the one of the plaque or the non-plaque site, for which the region of interest is set by the region-of-interest setting unit.

[8] The ultrasound diagnostic apparatus according to any one of [1] to [7], further comprising:
  an ultrasound probe; and
  an image acquisition unit configured to acquire the ultrasound image using the ultrasound probe.

[9] A control method for an ultrasound diagnostic apparatus, comprising:

detecting at least one detection target captured in an ultrasound image; and setting, in a case where a plurality of the detection targets are detected, only for a part of the detection target among the plurality of detection targets, a region of interest including the part of the detection target.

According to the present invention, there is provided an ultrasound diagnostic apparatus comprising: a detection target detection unit configured to detect at least one detection target captured in an ultrasound image; and a region-of-interest setting unit configured to set, in a case where a plurality of the detection targets are detected by the detection target detection unit, only for a part of the detection target among the plurality of detection targets, a region of interest including the part of the detection target. Therefore, the user can easily and accurately perform a diagnosis.

DESCRIPTION OF THE PREFERRED EMBODIMENTS

Hereinafter, embodiments of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value, respectively.

In the present specification, "same" and "identical" include an error range generally allowed in the technical field.

Embodiment 1

Figure 1:
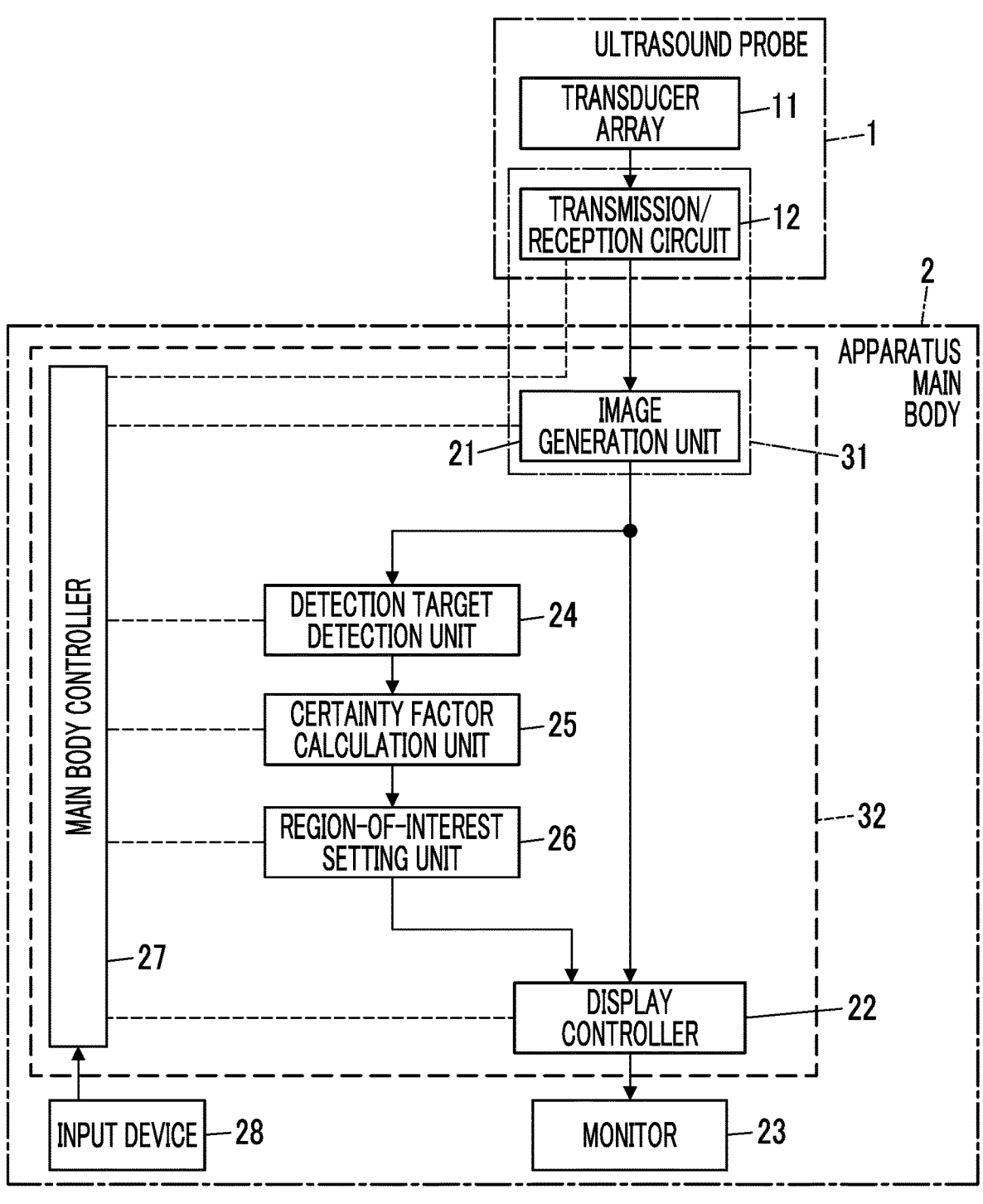
FIG. 1 is a block diagram showing a configuration of an ultrasound diagnostic apparatus according to Embodiment 1 of the present invention.

FIG. 1 shows a configuration of an ultrasound diagnostic apparatus according to Embodiment 1 of the present invention. The ultrasound diagnostic apparatus comprises an ultrasound probe 1 and an apparatus main body 2 connected to the ultrasound probe 1.

The ultrasound probe 1 includes a transducer array 11. A transmission/reception circuit 12 is connected to the transducer array 11.

The apparatus main body 2 includes an image generation unit 21 connected to the transmission/reception circuit 12 of the ultrasound probe 1. A display controller 22 and a monitor 23 are sequentially connected to the image generation unit 21. In addition, a detection target detection unit 24, a certainty factor calculation unit 25, and a region-of-interest setting unit 26 are sequentially connected to the image generation unit 21. The region-of-interest setting unit 26 is connected to the display controller 22. In addition, a main body controller 27 is connected to the transmission/reception circuit 12, the image generation unit 21, the display controller 22, the detection target detection unit 24, the certainty factor calculation unit 25, and the region-of-interest setting unit 26. An input device 28 is connected to the main body controller 27.

In addition, the transmission/reception circuit 12 and the image generation unit 21 constitute an image acquisition unit 31. Further, the image generation unit 21, the display controller 22, the detection target detection unit 24, the certainty factor calculation unit 25, the region-of-interest setting unit 26, and the main body controller 27 constitute a processor 32 for the apparatus main body 2.

The transducer array 11 of the ultrasound probe 1 includes a plurality of ultrasound transducers one-dimensionally or two-dimensionally arranged. Each of these ultrasound transducers transmits an ultrasound wave in accordance with a drive signal supplied from the transmission/reception circuit 12 and receives an ultrasound echo from a subject under examination to output a signal based on the ultrasound echo. For example, each ultrasound transducer is composed of a piezoelectric material consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like, and electrodes formed at both ends of the piezoelectric material.

Figure 2:
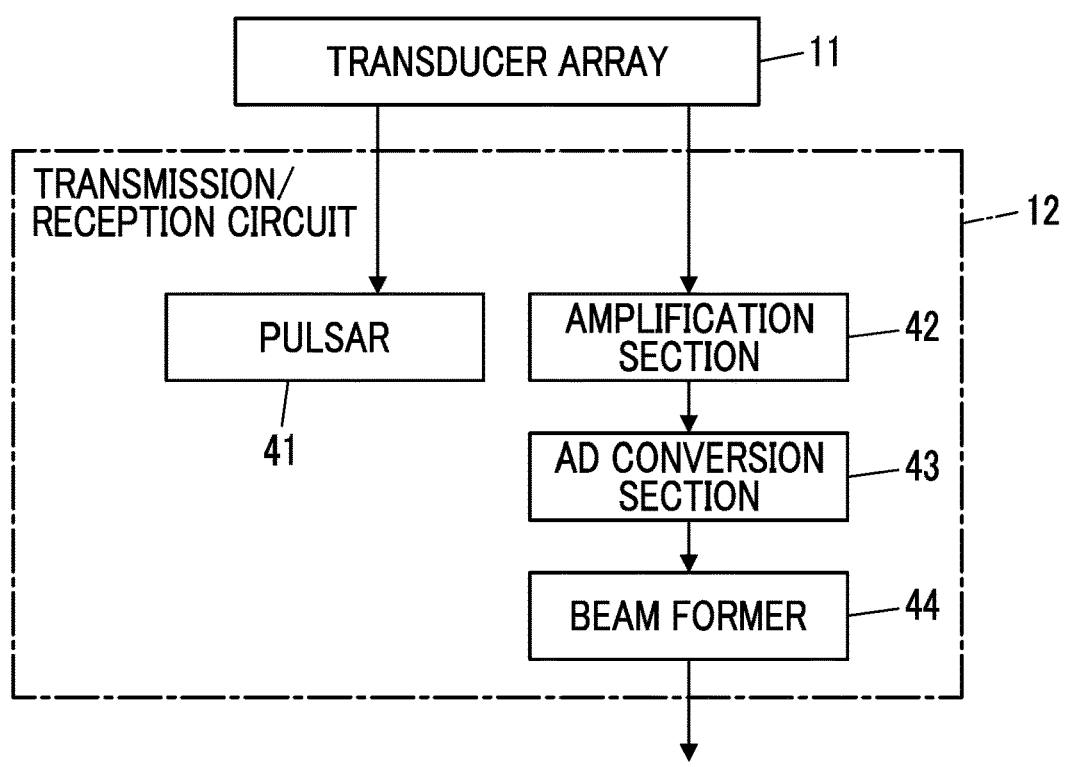
FIG. 2 is a block diagram showing a configuration of a transmission/reception circuit in Embodiment 1 of the present invention.

Under the control of the main body controller 27, the transmission/reception circuit 12 transmits the ultrasound wave from the transducer array 11 and generates a sound ray signal based on a reception signal acquired by the transducer array 11. As shown in FIG. 2, the transmission/reception circuit 12 includes a pulsar 41 connected to the transducer array 11, an amplification section 42, an analog-to-digital (AD) conversion section 43, and a beam former 44 that are sequentially connected in series to the transducer array 11.

The pulsar 41 includes, for example, a plurality of pulse generators, and the pulsar 41 adjusts an amount of delay of each of drive signals and supplies the drive signals to the plurality of ultrasound transducers such that ultrasound waves transmitted from the plurality of ultrasound transducers of the transducer array 11 form an ultrasound beam based on a transmission delay pattern selected according to a control signal from the main body controller 27. In this way, in a case where a pulsed or continuous-wave voltage is applied to the electrodes of the ultrasound transducer of the transducer array 11, the piezoelectric material expands and contracts to generate pulsed or continuous-wave ultrasound wave from each of the ultrasound transducers, whereby an ultrasound beam is formed from the combined wave of these ultrasound waves.

The transmitted ultrasound beam is reflected in, for example, a target such as a site of the subject under examination and propagates toward the transducer array 11 of the ultrasound probe 1. The ultrasound echo propagating toward the transducer array 11 in this way is received by each of the ultrasound transducers constituting the transducer array 11. In this case, each of the ultrasound transducers constituting the transducer array 11 receives the propagating ultrasound echo to expand and contract to generate a reception signal, which is an electrical signal, and outputs these reception signals to the amplification section 42.

The amplification section 42 amplifies the signal input from each of the ultrasound transducers constituting the transducer array 11 and transmits the amplified signal to the AD conversion section 43. The AD conversion section 43 converts the signal transmitted from the amplification section 42 into digital reception data. The beam former 44 performs so-called reception focus processing by applying and adding a delay to each reception data received from the AD conversion section 43. By this reception focus processing, each reception data converted by the AD conversion section 43 is phase-added, and a sound ray signal in which the focus of the ultrasound echo is narrowed down is acquired.

Figure 3:
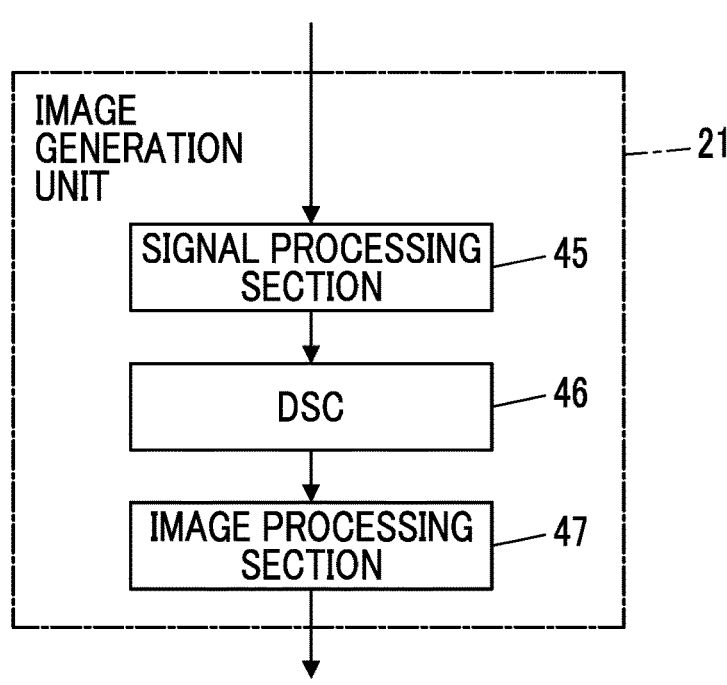
FIG. 3 is a block diagram showing a configuration of an image generation unit in Embodiment 1 of the present invention.

As shown in FIG. 3, the image generation unit 21 has a configuration in which a signal processing section 45, a digital scan converter (DSC) 46, and an image processing section 47 are sequentially connected in series.

The signal processing section 45 generates a B-mode image signal, which is tomographic image information regarding tissues inside the subject under examination, by performing, on the sound ray signal received from the transmission/reception circuit 12, correction of the attenuation due to the distance according to the depth of the reflection position of the ultrasound wave using a sound speed value set by the main body controller 27 and then performing envelope detection processing.

The DSC 46 converts (raster-converts) the B-mode image signal generated by the signal processing section 45 into an image signal according to a normal television signal scanning method.

The image processing section 47 performs various types of necessary image processing such as gradation processing on the B-mode image signal input from the DSC 46 and then sends the B-mode image signal to the display controller 22 and the detection target detection unit 24. Hereinafter, the B-mode image signal that has been subjected to image processing by the image processing section 47 is referred to as an ultrasound image.

Under the control of the main body controller 27, the display controller 22 performs predetermined processing on the ultrasound image or the like generated by the image generation unit 21 and displays the ultrasound image or the like on the monitor 23.

The monitor 23 performs various kinds of display under the control of the display controller 22. The monitor 23 can include a display device such as a liquid crystal display (LCD), or an organic electroluminescence (EL) display, for example.

The detection target detection unit 24 analyzes the ultrasound image generated by the image generation unit 21 to detect at least one detection target captured in the ultrasound image. The detection target detection unit 24 stores, for example, a plurality of template images for each of a plurality of detection targets and can detect the detection target by searching within the ultrasound image according to a so-called template matching method using the plurality of template images.

In addition, the detection target detection unit 24 includes, for example, a machine learning model that has learned a large number of ultrasound images showing the plurality of detection targets, respectively, and can also use this machine learning model to detect the detection target shown in the ultrasound image. In this case, the detection target detection unit 24 can output intermediate numerical data, which is generally called a feature amount in the field of machine learning, for each detection target.

Figure 4:
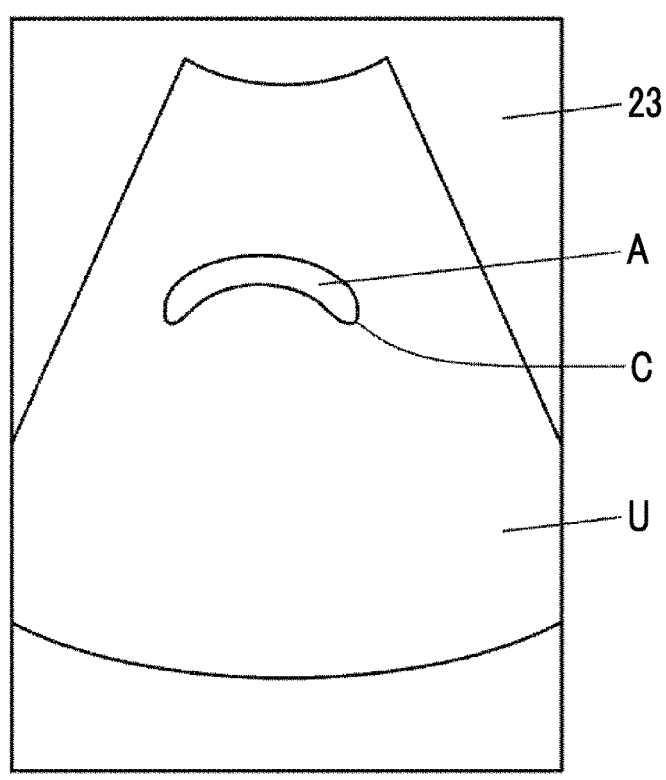
FIG. 4 is a diagram showing a contour line of a detection target.

For example, as shown in FIG. 4, the detection target detection unit 24 can output a contour line C of a detection target A in an ultrasound image U as a detection result.

Figure 5:
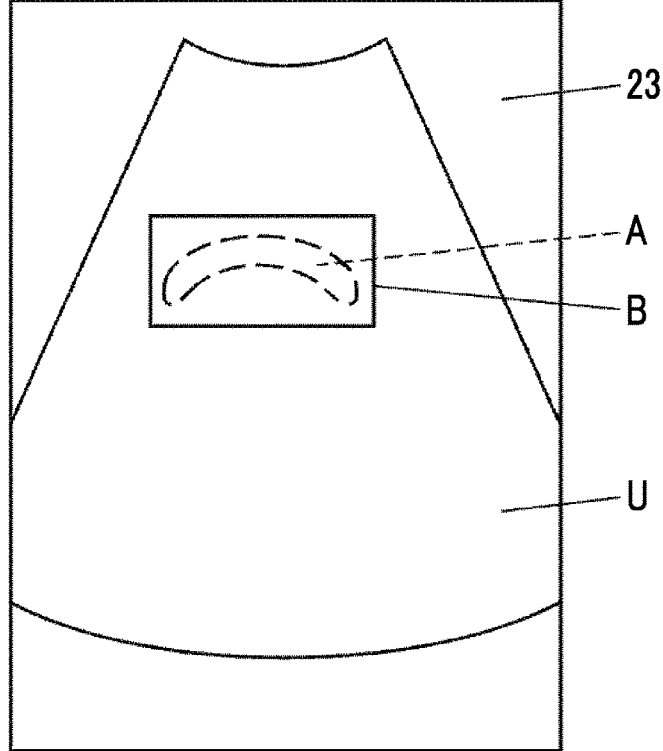
FIG. 5 is a diagram showing an image region including the detection target.

Instead of outputting the contour line C of the detection target A as the detection result, the detection target detection unit 24 can also output a rectangular image region B including the detection target A as the detection result, as shown in FIG. 5, for example. In this case, in order to accurately specify a position of the detection target A in a depth direction, it is preferable that a length of the image region B in the depth direction is at least 1 time and less than 2 times a length of the detection target A in the depth direction.

The certainty factor calculation unit 25 calculates a certainty factor for at least one detection target A detected by the detection target detection unit 24. Here, the certainty factor for the detection target A refers to an index indicating the degree of certainty for the detection result with respect to the detection target A, and can be calculated as a numerical value, for example. In a case where the detection target detection unit 24 detects the detection target A by template matching, the certainty factor calculation unit 25 can calculate the certainty factor for the detection target A by using, for example, similarity between a template image and a portion determined to represent the detection target A in the ultrasound image U. In a case where the detection target detection unit 24 detects the detection target A using the machine learning model, the certainty factor calculation unit 25 can also calculate the certainty factor for the detection target A, for example, based on the feature amount output from the detection target detection unit 24 for each detection target A.

Meanwhile, in general, in a case where the detection target A is automatically detected, a plurality of detection targets A that should not be depicted together in the ultrasound image, such as a feces and a minor axis image of an empty rectum, may be detected together in some ultrasound images on which detection processing is performed. In this case, a user such as a doctor may not be able to accurately grasp the detection target A in the ultrasound image, which may make it difficult to easily and accurately perform the diagnosis related to the detection target A. Here, the minor axis image of the rectum refers to a cross-sectional image of the rectum taken along a direction substantially orthogonal to a longitudinal direction of the rectum.

In a case where the plurality of detection targets A are detected by the detection target detection unit 24, the region-of-interest setting unit 26 sets, only for a part of the detection target A among the plurality of detection targets A, the region of interest including the part of the detection target A in order to allow the user such as a doctor to accurately grasp the detection target A.

Figure 6:
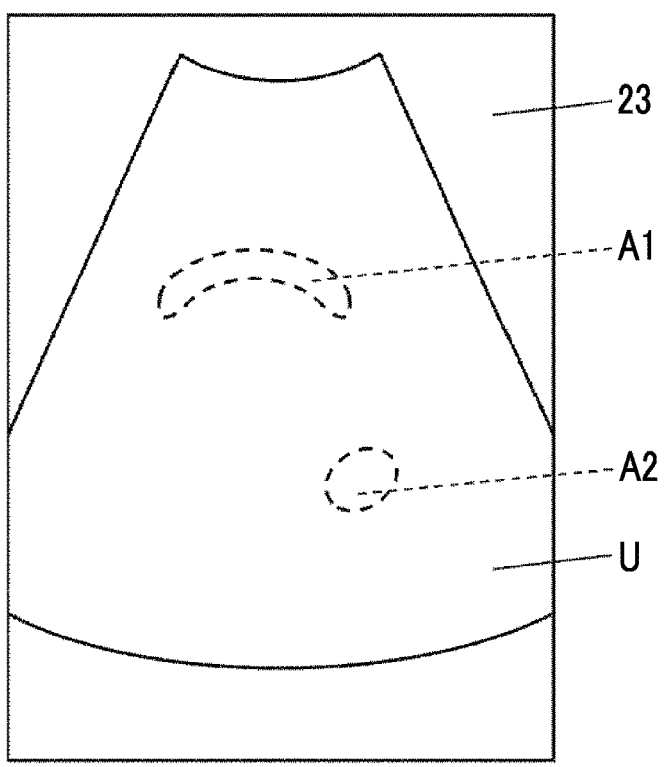
FIG. 6 is a diagram showing an example of an ultrasound image in which both a feces and an empty rectum are detected.
Figure 7:
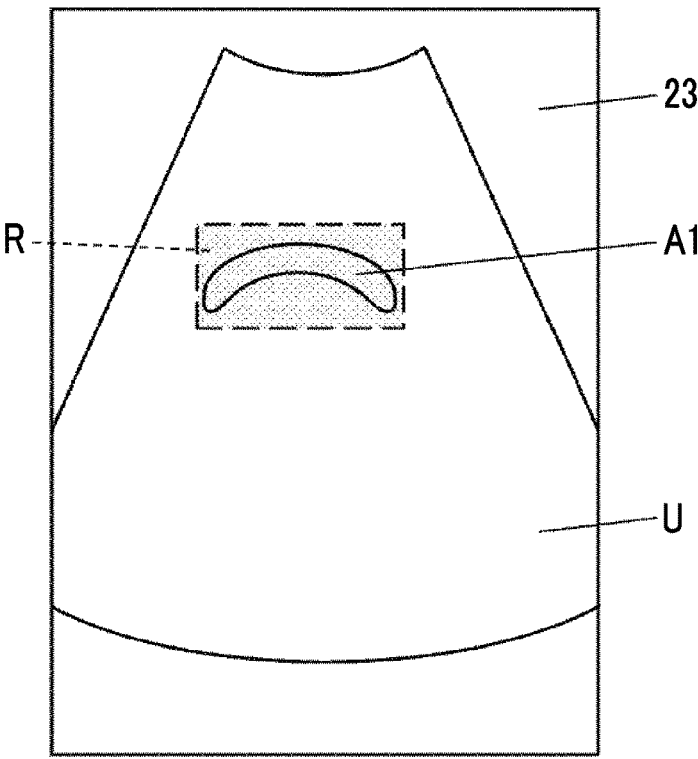
FIG. 7 is a diagram showing an example of a region of interest set for the feces shown in the ultrasound image.

For example, in a case where the detection target detection unit 24 detects both a feces A1 and an empty rectum A2 as the detection targets A as shown in FIG. 6, the regionof-interest setting unit 26 can refer to the certainty factor calculated for each of the feces A1 and the rectum A2 by the certainty factor calculation unit 25 to set a region of interest R for the detection target A having a higher certainty factor, as shown in FIG. 7. In FIG. 7, the rectangular region of interest R including only the feces A1 among the feces A1 and the rectum A2 is set.

In a case where the detection target detection unit 24 outputs the contour line C of the detection target A, the region-of-interest setting unit 26 sets, for example, a rectangular region that includes the contour line C and that circumscribes the contour line C, and enlarges the rectangular region by a magnification of at least 1 time and less than 2 times, for example, by a magnification of 1.2 times, while fixing the position of the center of gravity of the rectangular region, whereby the region of interest R can be set.

In addition, in a case where the detection target detection unit 24 outputs the image region B including the detection target A instead of outputting the contour line C of the detection target A, the region-of-interest setting unit 26 can set the image region B as the region of interest R.

The region of interest R set by the region-of-interest setting unit 26 in this manner can be displayed on the monitor 23, for example, with a closed frame line representing an edge of the region of interest R. The user such as a doctor can confirm the detection target A shown in the ultrasound image U by confirming the region of interest R displayed on the monitor 23.

The main body controller 27 controls each unit of the apparatus main body 2 and the ultrasound probe 1 in accordance with a program recorded in advance, or the like.

The input device 28 accepts an input operation by an examiner and sends input information to the main body controller 27. The input device 28 is composed of, for example, a device for the examiner to perform an input operation, such as a keyboard, a mouse, a trackball, a touchpad, or a touch panel.

Although the processor 32 including the image generation unit 21, the display controller 22, the detection target detection unit 24, the certainty factor calculation unit 25, the region-of-interest setting unit 26, and the main body controller 27 may be composed of a central processing unit (CPU) and a control program for causing the CPU to perform various types of processing, the processor 32 may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the image generation unit 21, the display controller 22, the detection target detection unit 24, the certainty factor calculation unit 25, the region-of-interest setting unit 26, and the main body controller 27 of the processor 32 can also be configured by being integrated partially or entirely into one CPU or the like.

Next, an example of an operation of the ultrasound diagnostic apparatus according to Embodiment 1 will be described with reference to the flowchart of FIG. 8.

First, in step S1, the ultrasound image U is acquired by the image acquisition unit 31. In this case, the transducer array 11 of the ultrasound probe 1 transmits the ultrasound beam into the subject under examination and receives the ultrasound echo from the inside of the subject under examination, whereby the reception signal is generated. The transmission/reception circuit 12 of the image acquisition unit 31 performs so-called reception focus processing on the reception signal to generate the sound ray signal, under the control of the main body controller 27. The sound ray signal generated by the transmission/reception circuit 12 is sent to the image generation unit 21. The image generation unit 21 generates the ultrasound image U using the sound ray signal sent from the transmission/reception circuit 12.

Next, in step S2, the detection target detection unit 24 analyzes the ultrasound image U acquired in step S1 to detect the detection target A shown in the ultrasound image U. In this case, the detection target detection unit 24 can detect the detection target A using a template matching method and can detect the detection target A using a machine learning model that has learned in advance a large number of ultrasound images U showing the detection targets A.

In step S3, the main body controller 27 determines whether or not the plurality of detection targets A are detected in step S2. As shown in FIG. 6, in a case where it is determined in step S3 that the plurality of detection targets A, such as the feces A1 and the rectum A2, are detected, the process proceeds to step S4.

In step S4, the certainty factor calculation unit 25 calculates the certainty factors for the plurality of detection targets A detected in step S2. In a case where the detection target A is detected in step S2 by template matching, the certainty factor calculation unit 25 can calculate the certainty factor for the detection target A by using, for example, the similarity between the template image and the portion determined to represent the detection target A in the ultrasound image U. Further, in a case where the detection target A is detected in step S2 using the machine learning model, the certainty factor calculation unit 25 can also calculate the certainty factor for the detection target A, for example, based on the feature amount output from the detection target detection unit 24 for each detection target A.

In step S5, the region-of-interest setting unit 26 sets the region of interest R for a part of the detection target A among the plurality of detection targets A detected in step S2. For example, in a case where the feces A1 and the rectum A2 are detected in step S2 as the detection targets A as shown in FIG. 6, the region-of-interest setting unit 26 can refer to the certainty factor calculated in step S3 for each of the feces A1 and the rectum A2 to set the region of interest R for the detection target A having a higher certainty factor among the feces A1 and the rectum A2. For example, in a case where the certainty factor for the feces A1 is higher than the certainty factor for the rectum A2, the region-of-interest setting unit 26 can set the region of interest R for the feces A1 as shown in FIG. 7, for example.

The region of interest R set in step S5 is sent to the display controller 22 and can be displayed on the monitor 23, for example, with a closed frame line representing the edge of the region of interest R.

In this way, since the region-of-interest setting unit 26 sets the region of interest R only for a part of the detection target A among the plurality of detection targets A detected in step S2, the user can easily and accurately grasp the detection target A shown in the ultrasound image U by confirming the region of interest R particularly even in a case where a plurality of detection targets A that should not be originally shown together in the ultrasound image U, such as the feces A1 and the minor axis image of the rectum A2, are detected together in step S2.

Further, in a case where it is determined in step S3 that only one detection target A is detected in step S2, the process proceeds to step S6. In step S6, the region-of-interest setting unit 26 sets the region of interest R for the one detection target A detected in step S2. The region of interest R set in step S6 can be displayed on the monitor 23 in the same manner as the region of interest R set in step S5.

Figure 8:
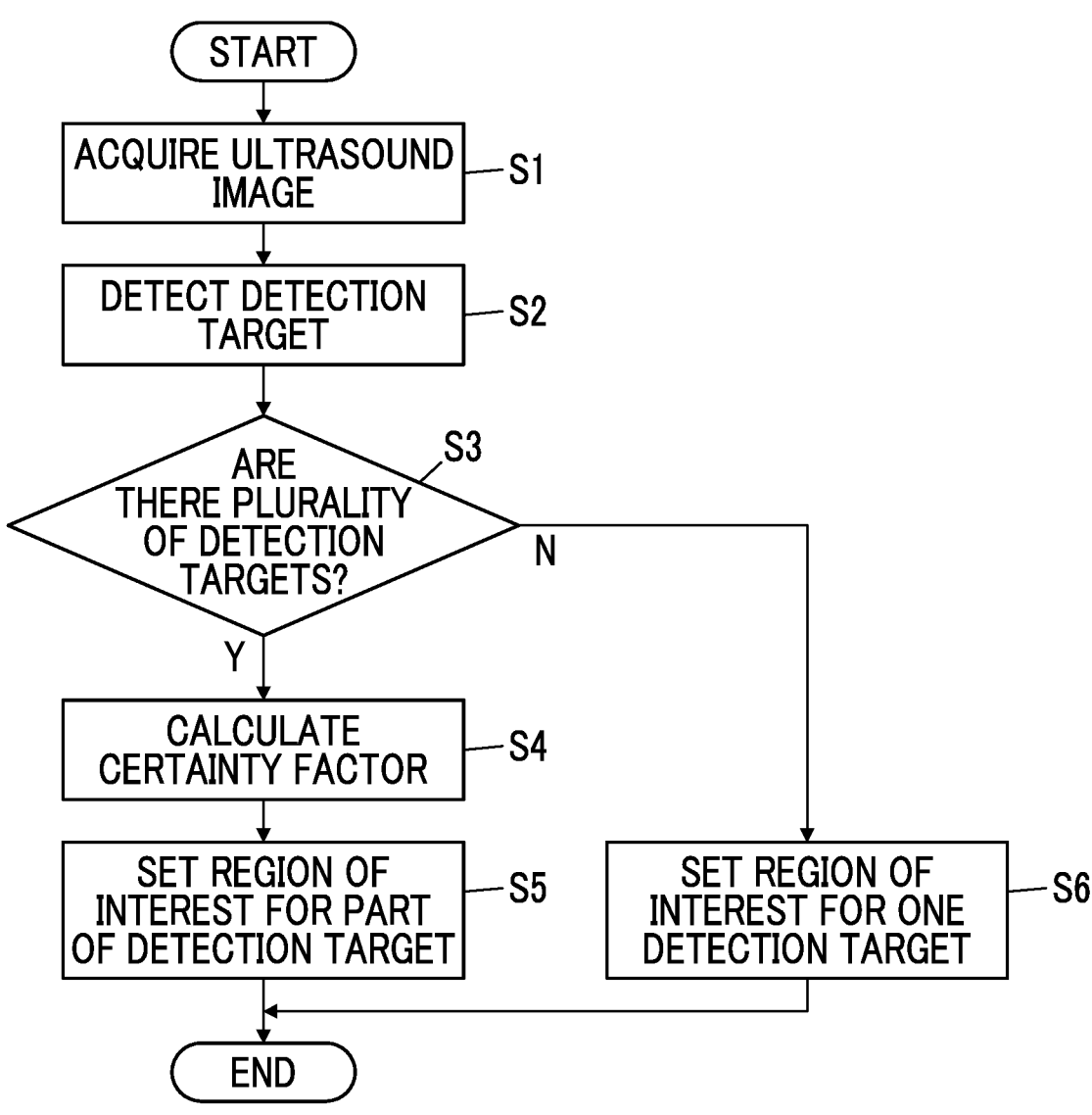
FIG. 8 is a flowchart showing an operation of the ultrasound diagnostic apparatus according to Embodiment 1 of the present invention.

In a case where the processing of step S5 or step S6 is completed in this manner, the operation of the ultrasound diagnostic apparatus shown in FIG. 8 is completed.

As described above, with the ultrasound diagnostic apparatus according to Embodiment 1 of the present invention, the detection target detection unit 24 detects at least one detection target A captured in the ultrasound image U, and the region-of-interest setting unit 26 sets, in a case where the plurality of detection targets A are detected by the detection target detection unit 24, only for a part of the detection target A among the plurality of detection targets A, the region of interest R including the part of the detection target A. Therefore, the user such as a doctor can easily and accurately perform the diagnosis related to the detection target A by accurately grasping the detection target A shown in the ultrasound image U.

Although a case where the transmission/reception circuit 12 is provided in the ultrasound probe 1 has been described, the transmission/reception circuit 12 may be provided in the apparatus main body 2.

Further, although a case where the image generation unit 21 is provided in the apparatus main body 2 has been described, the image generation unit 21 may be provided in the ultrasound probe 1.

In addition, the apparatus main body 2 may be a so-called stationary type, a portable type that is easy to carry, or a so-called handheld type that is composed of, for example, a smartphone or a tablet type computer. As described above, the type of the device that constitutes the apparatus main body 2 is not particularly limited.

In addition, the apparatus main body 2 can also comprise an image memory (not shown) that stores the ultrasound image U generated by the image generation unit 21 for each examination. In this case, the processing of steps S2 to S6 in the flowchart of FIG. 8 can also be performed, for example, on the ultrasound image U acquired in the past examination and stored in the image memory based on the user's instruction via the input device 28.

In addition, the apparatus main body 2 can also comprise an image input unit (not shown) for inputting the ultrasound image U from an external device (not shown). In this case, the processing of steps S2 to S6 in the flowchart of FIG. 8 can also be performed, for example, on the ultrasound image U input from the external device via the image input unit based on the user's instruction via the input device 28.

Further, a case where the region of interest R set by the region-of-interest setting unit 26 has a rectangular shape has been described, but the shape of the region of interest R is not limited to the rectangular shape and can be any shape, such as a circular shape and a polygonal shape.

Further, although a case where the region of interest R is displayed on the monitor 23 with a closed frame line representing the edge of the region of interest R has been described, the display mode of the region of interest R is not particularly limited. For example, only a part of the line representing the edge of the region of interest R may be displayed. For example, in a case where the region of interest R has a rectangular shape, only four corner portions of the line representing the edge of the rectangular shape can also be displayed.

In addition, the detection target detection unit 24 can also detect the detection target A through a machine learning model constructed by using a machine learning library called a so-called TensorFlow or a so-called Keras. In a case where the detection target A is detected by such a machine learning model, the detection target detection unit 24 can also output the certainty factor for each detection target A together with the detection target A. In this case, the certainty factor calculation unit 25 can send the certainty factor output by the detection target detection unit 24 to the region-of-interest setting unit 26 as it is without calculating the certainty factor again.

In addition, examples of the plurality of detection targets A detected by the detection target detection unit 24 include the feces A1 and the rectum A2, but the type of the detection target A is not particularly limited thereto.

Examples of the plurality of detection targets A to be detected by the detection target detection unit 24 also include a prostate and a uterus, for example. Normally, since the prostate is an organ present in a male body and the uterus is an organ present in a female body, the prostate and the uterus are not shown together in the ultrasound image U. Even in a case where both the prostate and the uterus are detected by the detection target detection unit 24, the region-of-interest setting unit 26 can set the region of interest R for any one of the prostate or the uterus, for example, based on the certainty factor calculated by the certainty factor calculation unit 25. By confirming the set region of interest R, the user such as a doctor can accurately grasp the type and the position of the detection target A and easily and accurately diagnose the subject under examination.

Here, an example has been described in which the region-of-interest setting unit 26 sets the region of interest R only for one detection target A among the two detection targets A detected by the detection target detection unit 24, but the region of interest R can also be set only for a part of the detection target A among three or more detection targets A detected by the detection target detection unit 24.

In this case, examples of the plurality of detection targets A to be detected by the detection target detection unit 24 include a so-called plaque generated in a blood vessel and a non-plaque site which is a site in a blood vessel where no plaque is generated, for example. In general, among so-called intima-media thicknesses (IMTs), a so-called max-IMT, which is the thickest IMT, may be measured based on the ultrasound image. In a case where a plaque is generated in a blood vessel, the maxIMT is usually measured by measuring the IMT of a site where the plaque is generated. A plurality of plaques and a plurality of non-plaque sites may be shown together in the ultrasound image U. In this case, in a case where the plurality of plaques and the plurality of non-plaque sites are detected, it may be difficult for the user to determine an appropriate measurement position.

In a case where a plurality of detection targets A consisting of the plurality of plaques and the plurality of non-plaque sites are detected by the detection target detection unit 24, the region-of-interest setting unit 26 can set the region of interest R, for example only for the plurality of plaques among the plurality of detection targets A. As a result, the user can easily grasp, for example, an appropriate measurement position of the maxIMT and easily and accurately perform subsequent measurement and diagnosis.

Embodiment 2

It is also possible to perform weighting on the certainty factor calculated by the certainty factor calculation unit 25 based on an input operation by the user via the input device 28.

Figure 9:
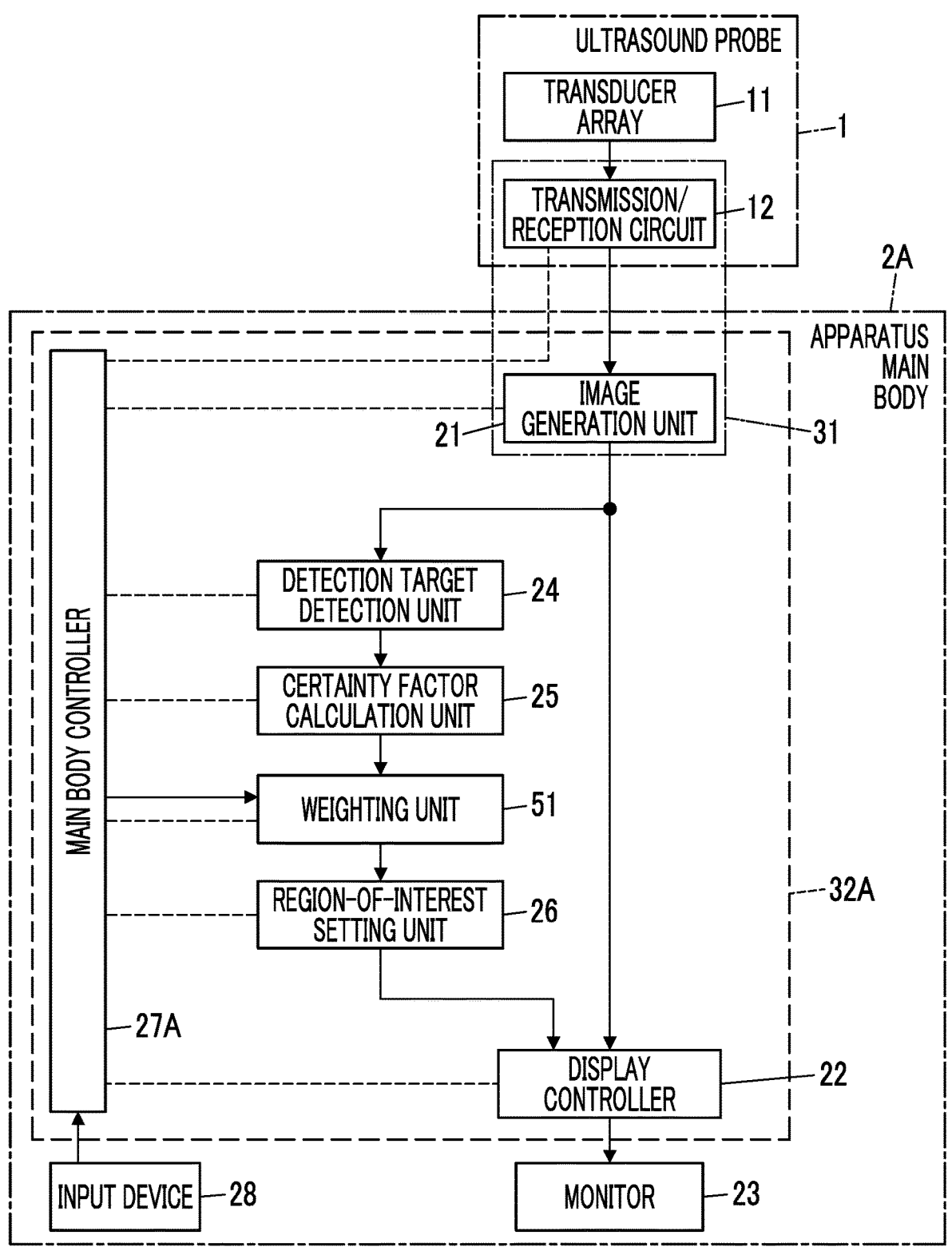
FIG. 9 is a block diagram showing a configuration of an ultrasound diagnostic apparatus according to Embodiment 2 of the present invention.

FIG. 9 shows a configuration of an ultrasound diagnostic apparatus according to Embodiment 2. The ultrasound diagnostic apparatus of Embodiment 2 comprises an apparatus main body 2A instead of the apparatus main body 2 in the ultrasound diagnostic apparatus of Embodiment 1 shown in FIG. 1. The apparatus main body 2A is configured such that a weighting unit 51 is added, and the main body controller 27A is provided instead of the main body controller 27, with respect to the apparatus main body 2 in Embodiment 1.

In the apparatus main body 2A, the weighting unit 51 is connected to the certainty factor calculation unit 25. The region-of-interest setting unit 26 and the main body controller 27A are connected to the weighting unit 51. In addition, a processor 32A for the apparatus main body 2A is composed of the image generation unit 21, the display controller 22, the detection target detection unit 24, the certainty factor calculation unit 25, the region-of-interest setting unit 26, the main body controller 27A, and the weighting unit 51.

The weighting unit 51 performs weighting on the certainty factor calculated by the certainty factor calculation unit 25 based on an input operation of the user via the input device 28. For example, in a case where information indicating that a specific detection target A is preferentially detected is input by the user via the input device 28, the weighting unit 51 performs weighting such that the certainty factor for the specific detection target A input by the user is higher than the original certainty factor. More specifically, in a case where the certainty factor is calculated using a numerical value, the weighting unit 51 can perform weighting by adding a predetermined positive number or by multiplying a predetermined number larger than 1 with respect to the certainty factor for the specific detection target A input by the user.

As described above, with the ultrasound diagnostic apparatus of Embodiment 2, the weighting unit 51 performs weighting on the certainty factor calculated by the certainty factor calculation unit 25 based on the input operation of the user via the input device 28, which makes it easier for the user to set the region of interest R for the detection target A that the user wants to preferentially detect. As a result, even in a case where the detection accuracy with respect to the detection target A is lowered for some reason, such as in a case where the sharpness of the ultrasound image U is low, the user can easily grasp the desired detection target A.

The weighting unit 51 can also perform weighting on the certainty factor for the specific detection target A based on information on the subject under examination input by the user via the input device 28. For example, in a case where the sex of the subject under examination is input by the user, the weighting unit 51 can perform weighting on the certainty factor for the prostate in a case where the input sex is male, and can perform weighting on the certainty factor for the uterus in a case where the input sex is female. As a result, the region of interest R can be set more accurately for the detection target A shown in the ultrasound image U.

Embodiment 3

In a case where the detection target A to be detected by the detection target detection unit 24 is a plaque or a non-plaque site of a blood vessel, the IMT can also be automatically measured for the detected plaque or non-plaque site.

Figure 10:
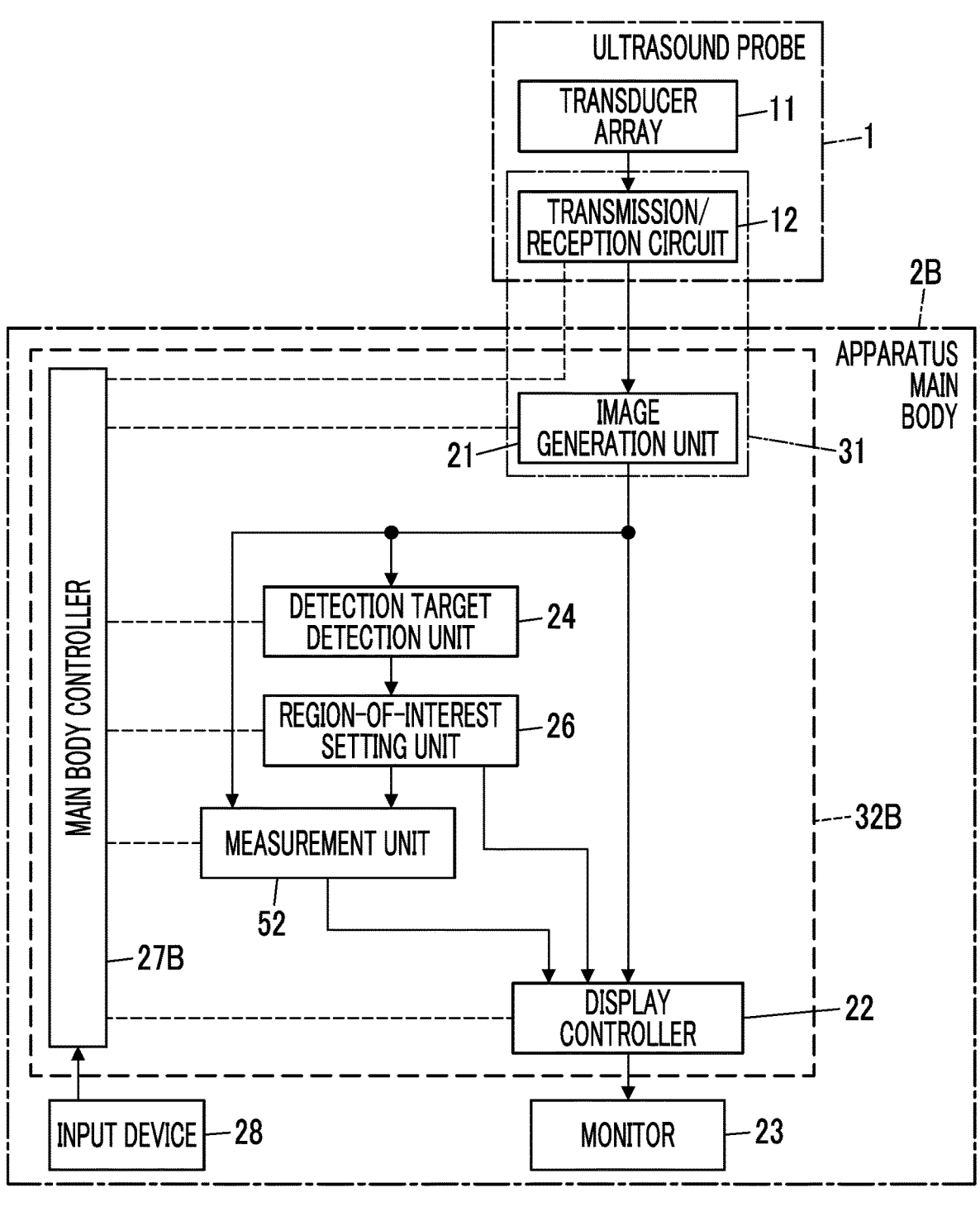
FIG. 10 is a block diagram showing a configuration of an ultrasound diagnostic apparatus according to Embodiment 3 of the present invention.

FIG. 10 shows a configuration of an ultrasound diagnostic apparatus according to Embodiment 3. The ultrasound diagnostic apparatus of Embodiment 3 comprises an apparatus main body 2B instead of the apparatus main body 2 in the ultrasound diagnostic apparatus of Embodiment 1 shown in FIG. 1. The apparatus main body 2B is configured such that the certainty factor calculation unit 25 is removed, a measurement unit 52 is added, and a main body controller 27B is provided instead of the main body controller 27, with respect to the apparatus main body 2 in Embodiment 1.

In the apparatus main body 2B, the measurement unit 52 is connected to the image generation unit 21 and the region-of-interest setting unit 26. In addition, the display controller 22 and the main body controller 27B are connected to the measurement unit 52. Further, a processor 32B for the apparatus main body 2B is composed of the image generation unit 21, the display controller 22, the detection target detection unit 24, the region-of-interest setting unit 26, the main body controller 27B, and the measurement unit 52.

The detection target detection unit 24 performs processing of detecting a plaque and a non-plaque site of a blood vessel as the detection targets A.

The region-of-interest setting unit 26 sets the region of interest R for one of the plaque or the non-plaque site of the blood vessel according to the detection result of the detection target detection unit 24. In this case, the region-of-interest setting unit 26 can set, for example, in a case where the plaque of the blood vessel is detected by the detection target detection unit 24, the region of interest R for the detected plaque, and can set, in a case where only the non-plaque site is detected instead of the plaque of the blood vessel by the detection target detection unit 24, the region of interest R for the detected non-plaque site. As a result, for example, the region of interest R can be automatically set at a portion suitable for measuring the maxIMT of the blood vessel.

The measurement unit 52 automatically measures, based on the ultrasound image U, the IMT of one of a blood vessel portion where the plaque is located or the non-plaque site, for which the region of interest R is set by the region-of-interest setting unit 26. The measurement result of the IMT by the measurement unit 52 is sent to the display controller 22 and displayed on the monitor 23, for example, as a numerical value. As a result, the user can easily confirm the maxIMT of the blood vessel.

As described above, with the ultrasound diagnostic apparatus of Embodiment 3, the region-of-interest setting unit 26 sets the region of interest R for one of the plaque or the non-plaque site of the blood vessel according to the detection result in the detection target detection unit 24, and the measurement unit 52 automatically measures the IMT of the one of the blood vessel portion where the plaque is located or the non-plaque site, for which the region of interest R is set by the region-of-interest setting unit 26, based on the ultrasound image U. Therefore, the user can easily confirm, for example, the maxIMT of the blood vessel and easily diagnose the subject under examination.

With respect to the ultrasound diagnostic apparatus of Embodiment 1 shown in FIG. 1 and the ultrasound diagnostic apparatus of Embodiment 2 shown in FIG. 9, the measurement unit 52 can also be provided in the apparatus main bodies 2 and 2A, as in the ultrasound diagnostic apparatus of Embodiment 3. Even in a case where the ultrasound diagnostic apparatus has such an apparatus configuration, similarly to the ultrasound diagnostic apparatus of Embodiment 3, the measurement unit 52 automatically measures the IMT of the one of the blood vessel portion where the plaque is located or the non-plaque site, for which the region of interest R is set by the region-of-interest setting unit 26, based on the ultrasound image U. Therefore, the user can easily confirm, for example, the maxIMT of the blood vessel and easily diagnose the subject under examination.

EXPLANATION OF REFERENCES

1: ultrasound probe
2, 2A, 2B: apparatus main body
11: transducer array
12: transmission/reception circuit
21: image generation unit
22: display controller
23: monitor
24: detection target detection unit
25: certainty factor calculation unit
26: region-of-interest setting unit
27, 27A, 27B: main body controller
28: input device
31: image acquisition unit
32, 32A, 32B: processor
41: pulsar
42: amplification section
43: AD conversion section
44: beam former
45: signal processing section
46: DSC
47: image processing section
51: weighting unit
52: measurement unit
A: detection target
A1: feces
A2: rectum
B: image region
C: contour line
R: region of interest
U: ultrasound image

What is claimed is:

1. An ultrasound diagnostic apparatus comprising:
a processor configured to
    acquire a single ultrasound image frame,
    detect a plurality of detection targets within the single ultrasound image frame,
    calculate, for each of the plurality of detection targets, a certainty factor indicating a degree of certainty for its detection result,
    identify, based on a comparison among a plurality of certainty factors for the plurality of detection targets, one detection target having a greatest certainty factor within the single ultrasound image frame, and
    automatically superimpose, on the single ultrasound image frame, a geometrical figure indicating a region that encloses the one detection target and excludes any portion of all other detection targets among the plurality of detection targets.

2. The ultrasound diagnostic apparatus according to claim 1,
wherein the processor is further configured to perform weighting on the plurality of certainty factors based on an input operation of a user.

3. The ultrasound diagnostic apparatus according to claim 1,
wherein the plurality of detection targets are a rectum and a feces.

4. The ultrasound diagnostic apparatus according to claim 2,
wherein the plurality of detection targets are a rectum and a feces.

5. The ultrasound diagnostic apparatus according to claim 1,
wherein the plurality of detection targets are a prostate and a uterus.

6. The ultrasound diagnostic apparatus according to claim 2,
wherein the plurality of detection targets are a prostate and a uterus.

7. The ultrasound diagnostic apparatus according to claim 1,
wherein the plurality of detection targets are a plaque and a non-plaque site of a blood vessel.

8. The ultrasound diagnostic apparatus according to claim 2,
wherein the plurality of detection targets are a plaque and a non-plaque site of a blood vessel.

9. The ultrasound diagnostic apparatus according to claim 7,
wherein the processor is further configured to
    measure an intima-media thickness of the blood vessel based on the single ultrasound image frame,
    set the region of interest for one of the plaque or the non-plaque site, and
    measure an intima-media thickness of the one of the plaque or the non-plaque site, for which the region of interest is set.

10. The ultrasound diagnostic apparatus according to claim 8,
wherein the processor is further configured to
    measure an intima-media thickness of the blood vessel based on the single ultrasound image frame,
    set the region of interest for one of the plaque or the non-plaque site, and
    measure an intima-media thickness of the one of the plaque or the non-plaque site, for which the region of interest is set.

11. The ultrasound diagnostic apparatus according to claim 1, further comprising:
an ultrasound probe; and
wherein the processor is further configured to acquire the single ultrasound image frame using the ultrasound probe.

12. A control method for an ultrasound diagnostic apparatus, comprising:
acquiring a single ultrasound image frame;
detecting a plurality of detection targets within the single ultrasound image frame;
calculating, for each of the plurality of detection targets, a certainty factor indicating a degree of certainty for its detection result;
identifying, based on a comparison among a plurality of certainty factors for the plurality of detection targets, one detection target having a greatest certainty factor within the single ultrasound image frame; and
automatically superimposing, on the single ultrasound image frame, a geometrical figure indicating a region that encloses the one detection target and excludes any portion of all other detection targets among the plurality of detection targets.

13. The ultrasound diagnostic apparatus according to claim 1,
wherein the processor is configured to
    based on information input by a user and indicating that a specific detection target among the plurality of detection targets is preferentially detected, perform weighting on a certainty factor for the specific detection target, and automatically superimposing, on the single ultrasound image frame, the geometrical figure after weighting.

14. The ultrasound diagnostic apparatus according to claim 1, wherein the processor is configured to perform weighting on the plurality of certainty factors based information of a subject input by a user, and automatically superimposing, on the single ultrasound image frame, the geometrical figure after weighting.

\* \* \* \* \*